US007876433B2

(12) United States Patent
Joosten (10) Patent No.: US 7,876,433 B2
(45) Date of Patent: Jan. 25, 2011

(54) SPECTROMETER OPTICS COMPRISING POSITIONABLE SLOTS AND METHOD FOR THE FULLY AUTOMATIC TRANSMISSION OF CALIBRATING ADJUSTMENTS BETWEEN SPECTROMETERS EQUIPPED WITH OPTICS OF THIS TYPE

(75) Inventor: Heinz-Gerd Joosten, Kranenburg (DE)

(73) Assignee: Spectro Analytical Instruments GmbH, Kleve (DE)

( * ) Notice: Subject to any disclaimer, the term of this patent is extended or adjusted under 35 U.S.C. 154(b) by 577 days.

(21) Appl. No.: 11/721,847

(22) PCT Filed: Nov. 4, 2005

(86) PCT No.: PCT/EP2005/011844

§ 371 (c)(1),
(2), (4) Date: Apr. 7, 2008

(87) PCT Pub. No.: WO2006/063637

PCT Pub. Date: Jun. 22, 2006

(65) Prior Publication Data

US 2009/0284740 A1    Nov. 19, 2009

(30) Foreign Application Priority Data

Dec. 16, 2004    (DE) .................. 10 2004 061 178

(51) Int. Cl.
*G01J 3/28* (2006.01)
(52) U.S. Cl. .................................................. 356/326
(58) Field of Classification Search .......... 356/326–328
See application file for complete search history.

(56) References Cited

U.S. PATENT DOCUMENTS

| 4,027,975 | A | * | 6/1977 | Turner et al. ............... 356/334 |
| 4,340,303 | A | * | 7/1982 | Grisar et al. ............... 356/328 |
| 4,605,306 | A | * | 8/1986 | Kaffka et al. .............. 356/334 |
| 4,645,344 | A | * | 2/1987 | Thevenon ................... 356/328 |

OTHER PUBLICATIONS

International Preliminary Report on Patentability issued in corresponding Internetional Application No. PCT/EP2005/011844 issued on Feb. 20, 2008.
Corrected Version of International Preliminary Report on Patentability issued in corresponding International Application No. PCT/EP2005/011844 on Apr. 18, 2008 with English language translation.

* cited by examiner

*Primary Examiner*—Kara E Geisel
(74) *Attorney, Agent, or Firm*—Connolly Bove Lodge & Hutz LLP (57) ABSTRACT

The invention relates to spectrometer optics with a beam path from a beam source to a number of electro-optical sensors without spatial resolution, the beam path comprising an entry slot, a dispersive element, and a number of exit slots arranged on a focal curve, wherein furthermore:
a first actuator for changing the angle of incidence ε between the beam from the entry slot to the dispersive element and from the normal to the dispersive element;
a number of second actuators for moving the exit slots tangentially with respect to the focal curve or in a peripheral direction along the focal curve and
a controller which is adapted to control the first actuator and the second actuators to carry out a calibration
is provided.

5 Claims, 6 Drawing Sheets

SPECTROMETER OPTICS COMPRISING POSITIONABLE SLOTS AND METHOD FOR THE FULLY AUTOMATIC TRANSMISSION OF CALIBRATING ADJUSTMENTS BETWEEN SPECTROMETERS EQUIPPED WITH OPTICS OF THIS TYPE

CROSS REFERENCE TO RELATED APPLICATION

The present application is a national stage application of PCT/EP2005/011844, filed Nov. 4, 2005, which claims priority from German Pat. Appl. No. 10 2004 061 178.5, filed Dec. 16, 2004.

The present invention relates to spectrometer optics with a beam path from a beam source to a number of electro-optical sensors without spatial resolution, as well as to a method for calibrating spectrometer systems.

Figure 1:
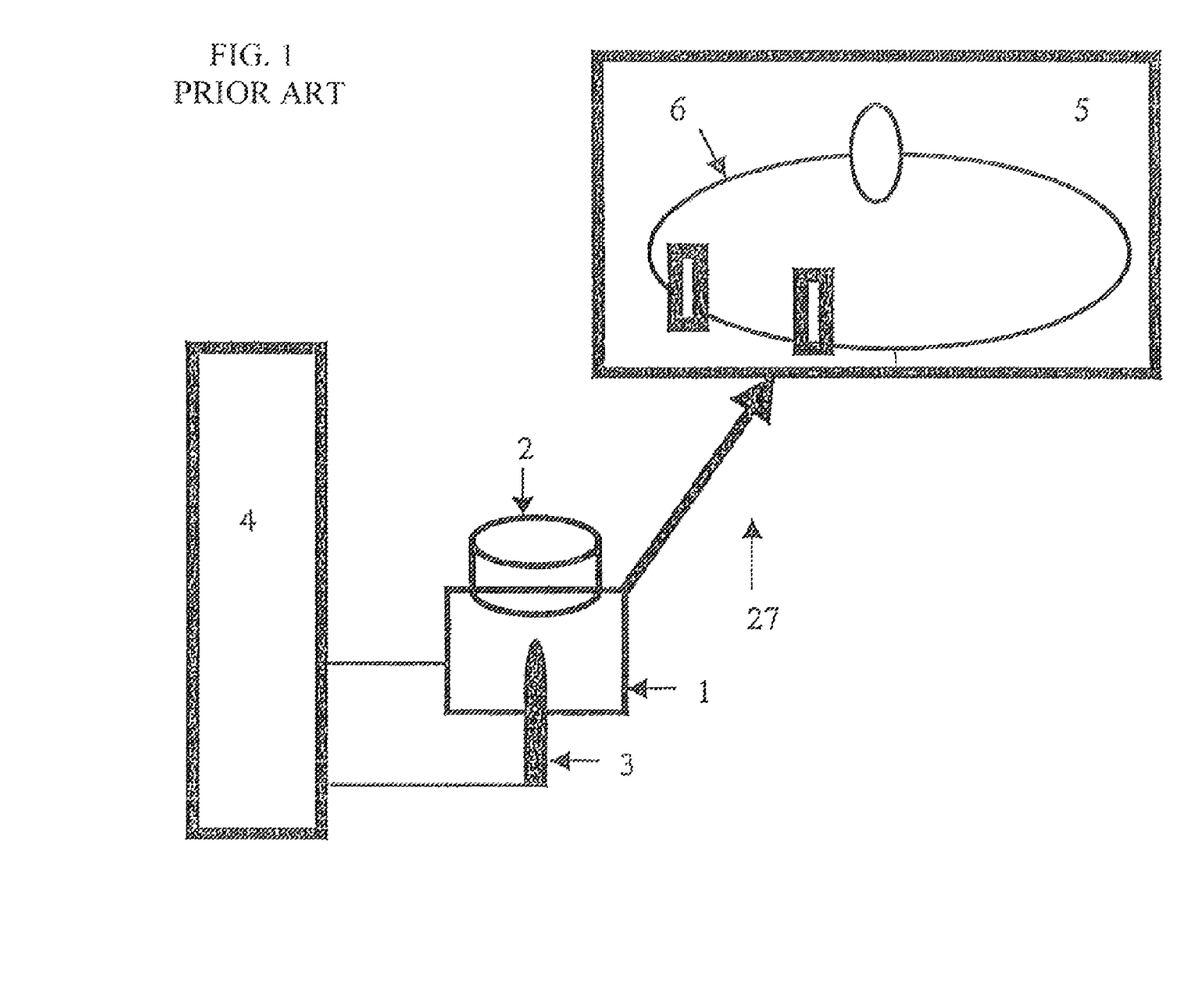
FIG. 1 shows a known spectrometer (prior art).

Emission spectrometers with spark and/or arc excitation are used in the multi-element routine analysis of metals. With the aid of a schematic diagram of the construction of such systems FIG. 1 shows the general prior art. The support (1)) allow a sample (2) to be supported at a spacing of 0.5 to 5 mm from a counter electrode (3). The excitation generator (4) firstly generates a high-voltage pulse which ionizes the atmosphere between sample surface and counter electrode (air or shielding gas) and thus renders it low-resistance. A direct current of 1 A to 10 A is then fed via the low-resistance spark gap in the case of an arc generator. This arc is maintained for a period of 0.5 s to 10 s.

Instead of a single long pulse the spark generator generates short pulses of 50 µs to 2 ms duration with a sequence frequency between 50 Hz and 800 Hz. A new trigger pulse is required before each individual spark. Thermal plasma is formed at temperatures between 4,000 K and 20,000 K in which plasma free atoms and ions are excited for emission of a line spectrum. The emitted light either passes via the direct light path or a fiber optic (27) into an optical system (5), on the focal curve (6) of which the spectral lines are sharply depicted.

Figure 2:
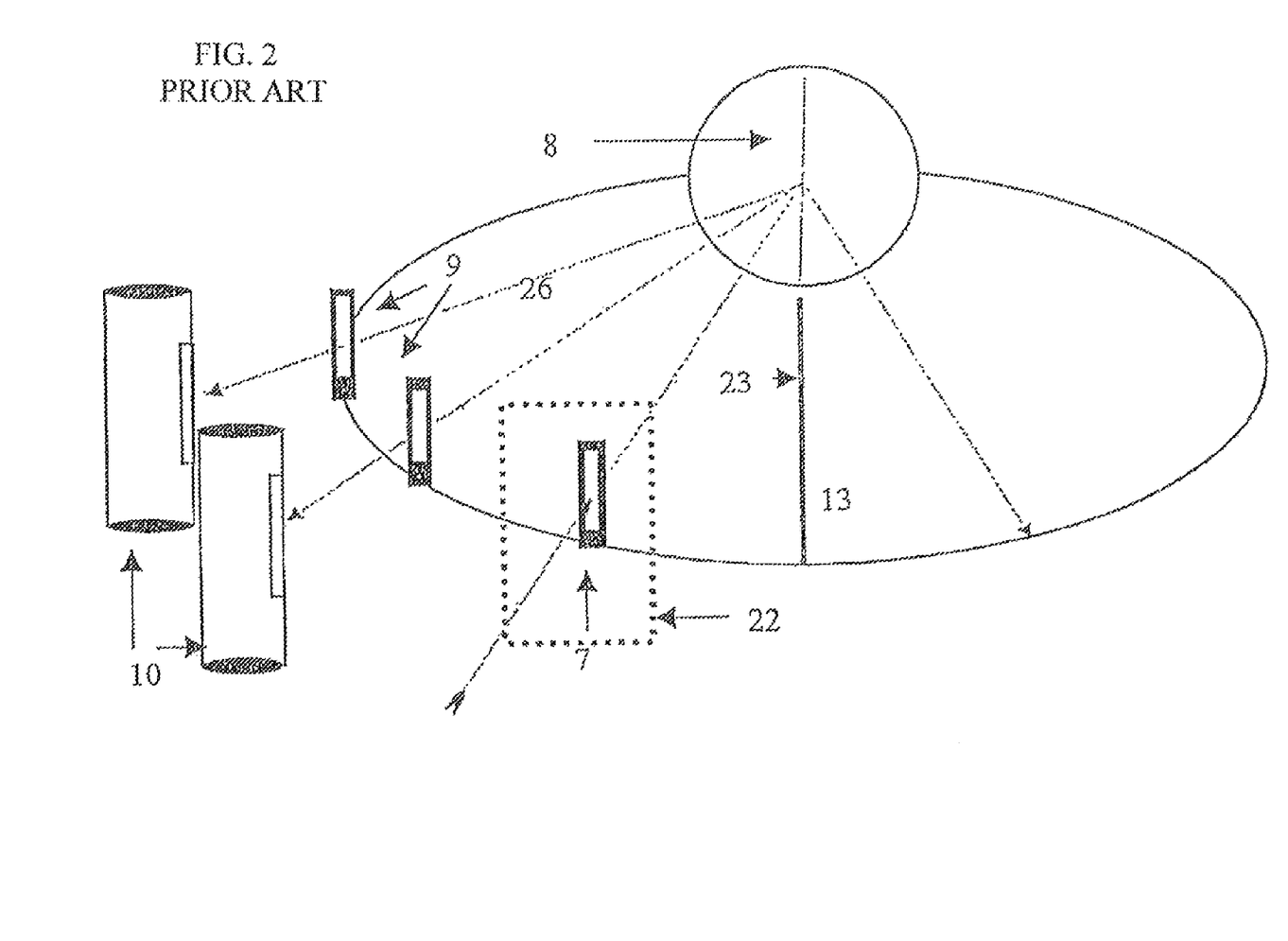
FIG. 2 shows a known spectrometer system (prior art).

Two methods of measuring the spectral lines sharply depicted on the focal curve are conventional at present:

1. FIG. 2 shows the first type of spectrometer systems which also constitute the prior art. The light strikes a concave grating (8) trough an entry slot (7). A spectrum is produced as a quantity of wavelength-dependent diffraction patterns of the entry slot. The spectral lines of interest are stopped down by exit slots (9) and their intensity is measured by means of multiplier phototubes (10).

Figure 3:
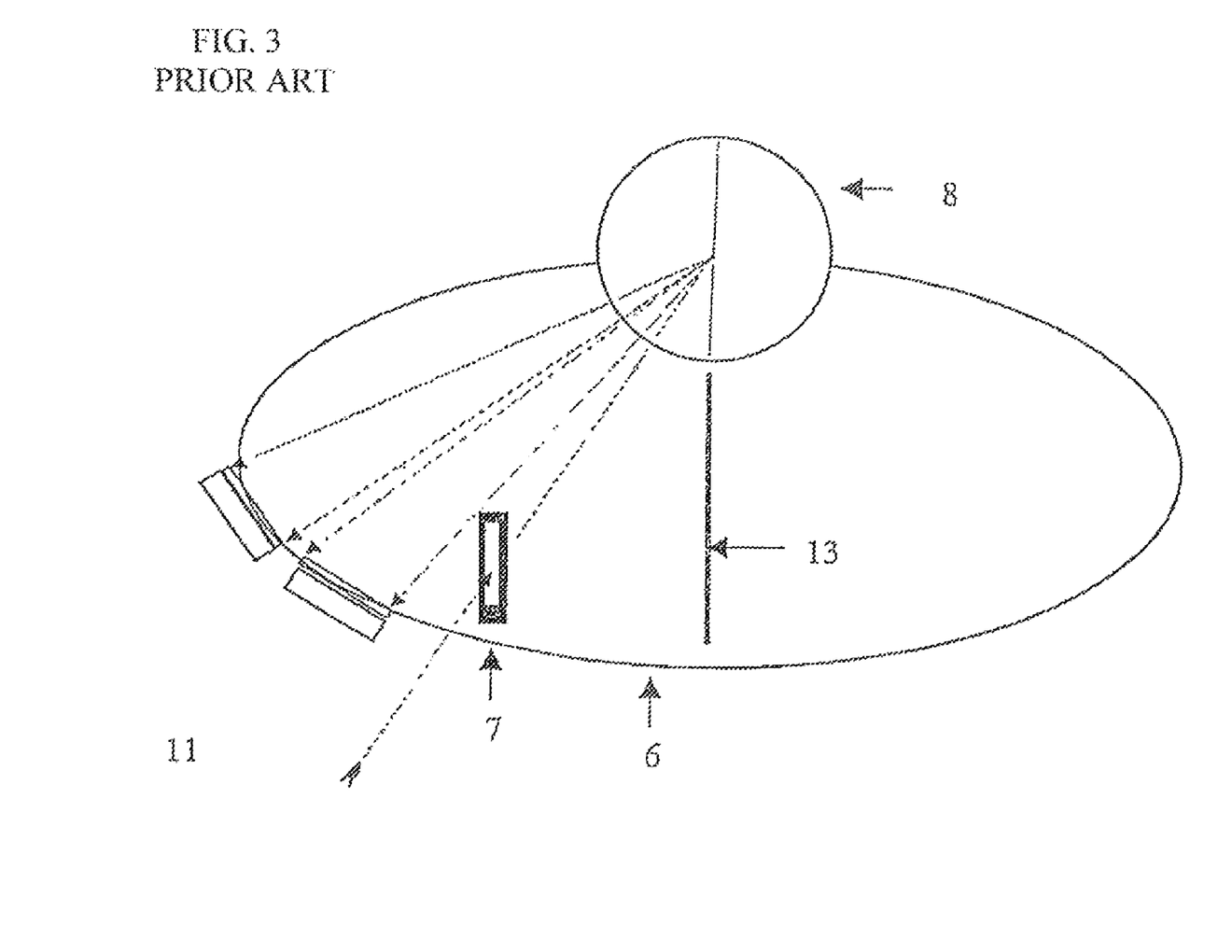
FIG. 3 shows a known spectrometer construction (prior art).

2. FIG. 3 outlines the second common spectrometer construction according to the prior art. The light strikes the grating (8) through an entry slot in this embodiment as well. Instead of individual exit slots however, multi-channel sensors (11) are assembled along the focal curve (6) here. These multi-channel sensors comprise a linearly arranged field of photo-sensitive sensor elements, what are known as pixels. In this construction simultaneous recording of complete spectral ranges is possible.

Calibration functions are accordingly determined for the spectral lines that are known as being suitable, which functions depict the measured values on element contents. In devices which, as described above under (1.), are equipped with exit slots, according to the prior art the calibration functions are determined for each device as a component of the production process.

For this purpose a set of standard samples is measured for each material group. A calibration polynomial is then specifically determined for each material group and element by way of a multi-variant regression calculation. A material group comprises material with similar chemical compositions. Examples of material groups are chromium steels, low-alloy steels or lead bronzes. Devices with measuring methods for more than thirty elements in more than twenty material groups are not unusual. Up to one hundred standard samples have to be measured per material group to determine the calibration functions.

In devices with extensive applications, measurement of the standards, determining the calibration functions and subsequent checking takes up more than a man-month of labor time. This labor input constitutes a considerable cost factor. The endeavor is therefore to simplify the calibration process.

The following method of resolution is followed in this connection.

The number of standards per material group is reduced to typically five to twenty standards. The constant and linear terms of the calibration polynomial and the greatest line and interelement interferences are re-determined using this reduced set of standard samples. The remaining variables are taken over from a "basic calibration". Considerably fewer calibration standards have to be measured with this procedure. The calibration continues to be checked by measurements of control samples however. The accuracies of basic calibration cannot be attained. This is due to the fact that interferers and polynomial coefficients have been determined by only a few standards (poorer statistical protection) or have been taken over from a basic calibration without re-calculation.

What is known as recalibration is carried out before the systems are used. In this case a maximum value and a minimum value are determined for each measuring channel by measuring two samples. The same samples were also measured at the instant of calibration.

A recalibration straight line can be determined from desired and actual values, by which line the calibration polynomial is "inclined" and "displaced". Linear changes to the calibration curve may be compensated thereby.

For the devices with full spectra detection described under item (2.), a method for calibration transmission from a reference device to any desired standard device constructed in the same way is known from German patent application DE 101 52 679. The method is successfully used as standard. In the case of CCD-based spectrometer systems it reduces the end test and calibration expenditure to the measurement of a single sample. This sample is called an adjustment sample. The basic idea of the method according to patent application DE 101 52 679 is the separation of the calibration function into a device-specific function $K_G$ and a device-independent calibration function $K_O$.

$$\text{Calculated contents} = K_O(K_G(\text{measured values}))$$

$K_G$ can accordingly be regarded as a function that is associated with a spectrometer system and which converts the spectra of this system into the spectra of the reference system. The calibration function $K_O$ is a conventional basic calibration of the type as has been described above. It is carried out once on any desired device, hereinafter called the reference device.

The function $K_G$ is accordingly completely automatically determined by detecting the spectrum of the adjustment sample for any desired device G. In this case G is a spectrometer with a construction identical to the reference device R but owing to manufacturing tolerances provides different raw spectra.

If any desired sample P is measured on G and the associated spectra $K_G$ is employed, the same spectrum is obtained as would have been obtained for P on R. From this it follows that the calibration functions $K_O$ of the reference device R may be used.

The necessity of an individual calibration of G is therefore dispensed with.

The use of $K_G$ comprises use of a sequence of sub-functions. The most important of these corrections steps are:

Correction of the Pixel Offset

The spectrum seems to be offset by a few pixels from one device to the next owing to unavoidable inaccuracies in adjustment. This pixel offset is not necessarily constant over the spectrum although there are no erratic changes but only constant ones.

The correction is made by placing the measured spectrum of the adjustment sample over the reference spectrum and the position of minimal difference is determined.

Correction of Resolution

The cell sensors are not located exactly on the focal curve over their entire width. The focal curve is always bent, even in the case of what is known as flat field-gratings in which the curve has been straightened in parts. The cell sensors are always linearly arranged however. This results in spreading of the spectral lines into the defocused regions. The resolution does not change erratically, similar spectral resolutions apply for closely adjacent wavelengths.

Intensity Correction

The optical conductance as a function of the wavelength varies from one spectrometer system to the next. Even during the life of a system this function is subject to constant variations. Reasons for this are sailing of optical interfaces, solarization effects (wavelength-dependent tarnishing) of components (particularly of fiber optics), changes in the atmosphere of spectrometer optics, variations in the grating diffraction efficiency, etc.

After using the above-described calculation steps this correction is carried out last since profile displacements and changes in resolution have to be taken into account beforehand.

The intensity correction consists of application of a function which provides a polynomial for each pixel or small pixel ranges. These polynomials allow conversion of intensities measured on G into intensities which would have been obtained at this location of the spectrum using reference device R. This intensity transmission function also changes only constantly over the wavelength.

The individual correction steps are described in detail in both patent application DE 101 52 579 and in the dissertation by the inventor "Verfahren zur automatisierten Übertragung von Emissionsspektrometer-Kalibrationen" (Method for automated transmission of emission spectrometer calibrations), Duisburg 2003.

It is important to maintain that pixel displacement, resolution and luminous intensity can be predicted at a location in the spectrum if these parameters are known for the environment of the location. This principle of locality is decisive for calibration transmission since it is not possible to find an adjustment sample, of which the spectrum contains each spectral line of potential interest.

Patent application DE 101 52 679 and the above-mentioned dissertation are limited to a method for calibration transmission for spectrometer systems that are equipped with multi-channel sensors. In systems of this type the spectral environment of the adjustment sample is available for a line that is to be recalibrated.

The method is not suitable for use with spectrometer systems which are equipped with exit slots instead of multi-element sensors. In this case only the locations of the spectrum at which the spectral lines of interest appear are measured. The spectral environment of these lines is not detected.

It is therefore the object of the present invention to configure spectrometer optics with sensors without spatial resolution in such a way that the spectral environment of the spectral lines to be measured can be detected. It is a further object of the present invention to create a method for fully automatic transmission of calibrations between spectrometers of this type.

This object is achieved by a spectrometer with a beam path from a beam source to a number of electro-optical sensors without spatial resolution, and by a method for calibrating spectrometer systems.

PRINCIPLE OF THE INVENTION

The starting point of the invention is the method described in patent application DE 101 52 679 which allows calibration transmission for spectrometer systems equipped with sensors with spatial resolution.

Since a first actuator is provided for changing the angle of incidence $\epsilon$ between the beam from the entry slot to the dispersive element and the normal to the disperse element, and a number of second actuators are provided for moving the exit slots tangentially to the focal curve or in the peripheral direction along the focal curve, and finally a controller is provided which is adapted to control the first actuator and the second actuators to carry out a calibration, the spectral environment of the lines to be measured can be detected and each exit slot can be moved into the position at which the sought line is to be expected.

Three steps need to be carried out to render any desired standard device G capable of producing the same measured values as a reference device R for any desired samples:

1. First of all a displacement vector on the focal plane (plane which is fixed by the mean grating height and the mean slot height) is determined for the entry slot and each exit slot of G. This vector indicates to where entry slot and exit slots have to be displaced, so the same wavelength segment with the same resolution passes through each exit slot of G as in the case of the corresponding exit slot of R. More precisely: the displacement vectors are determined in such a way that optimally similar wavelength segments with optimally similar resolution fall through the exit slots of G as through the slots of R. The correspondence rating is measured and an error message is output in the event of excessive differences.

2. Entry slot and exit slots are then moved by the previously determined vectors to the calculated desired positions via suitable positioning devices.

3. Finally, an intensity correction function (normally a polynomial) is determined for each exit slot $A_i$ and this allows the raw measured values measured with $A_i$ on G to be converted into measured values as would be obtained for the corresponding exit slot of R.

The coefficients for the intensity correction function are also determined such that faults in the optics, the electronic measuring devices, or the excitation generator of G are recognized.

As in patent application DE 101 52 679 a device-dependent calibration function $K_G$ is therefore used in this case as well. For a type of device with n exit slots the function is clearly characterized by the following vector $K'_G$:

$$K'_G = (x_e, y_a), (x_i, y_i), \ldots, (x_n, y_n), (a_{1,0}, \ldots, a_{1,m}), \ldots,$$
$$(a_{n,0}, \ldots, a_{n,m})) \, x_i, y_i, X_e, a_{1,i}, \in \Re \quad \text{Def. 1}$$

For each exit slot $A_i$ of G, $K'_G$ contains a number pair $(X_i, Y_i)$ that defines a vector on the focal plane which indicates to where $A_i$ has to be displaced in order to detect with $A_i$ the same spectral range with the same resolution as with the corresponding exit slot of R. A number pair $(X_e, Y_a)$ is also calculated that defines the necessary displacement of the entry slot on the focal plane. Finally, for each exit slot $A_i$, $K'_G$ contains an m-tuple $(a_{i,0} \ldots a_{i,m})$ that defines a polynomial of the m-th degree (intensity correction function). Once the entry and exit slots of G have been moved to the desired position the measured values of G are converted to the level of R using this intensity correction function.

It will be shown that the structure according to Def. 1 may be simplified to the following quantity:

$$K'_G = ((x_e, y_a), y_i, \ldots, y_n, (a_{1,0}, \ldots, a_{1,i}), \ldots,$$
$$(a_{n,0}, \ldots, a_{n,i}) \, x_1, y_i, x_e, a_{1,i}, \in \Re \quad \text{Def. 2}$$

For each exit slot, instead of one number pair that describes the position on the focal plane, only a difference from the current position in the direction of the focal curve is determined with $y_i$. $(X_o, Y_o)$ again describes the displacement vector of the entry slot.

Linear functions which are defined for each exit slot $A_i$ by the number pair $(a_{i,0}, a_{i,1})$ are usually sufficient as the intensity correction polynomials.

After determining $K'_G$ and subsequent adjustment of the slot position, the device G is ready to measure any desired samples. Measured value processing should then be expanded with respect to conventional measured value processing in that, immediately after detection, the raw measured value is inserted as an argument into the intensity correction function. Calculation then continues with the measured value modified by the correction function. It will be described in detail hereinafter how $K'_G$ is determined.

STATEMENT OF THE INVENTION

Step 1—Determining the Slot Displacement Vectors

To be able to determine the displacement vectors first of all the spectral environment around each exit slot must be rendered accessible. This is done in that the optical system is expanded to the extent that either the entry slot allows itself to be moved along the focal curve or, alternatively, a rotatable plane-parallel quartz plate is provided behind the entry slot.

Figure 4:
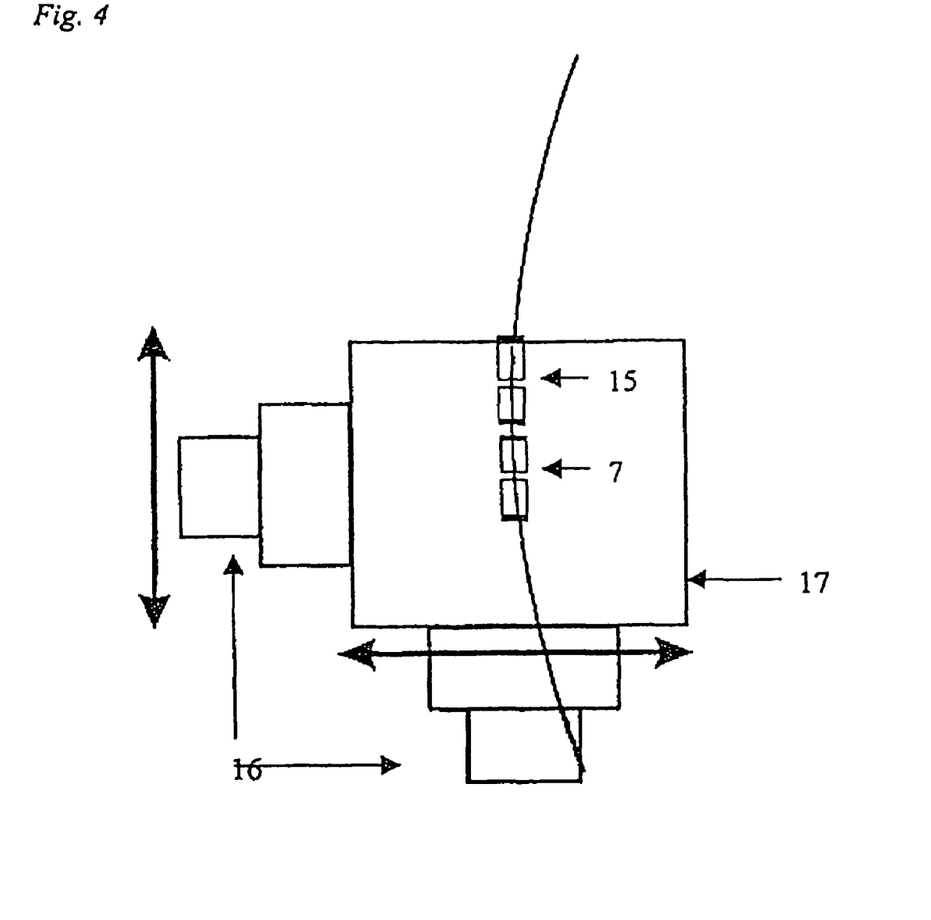
FIG. 4 illustrates an exemplary spectrometer having a moving entry slot.

FIG. 4 shows the principle for a moving entry slot. The entry slot region (22), marked in FIG. 2, of optics is shown in plan view. The entry slot (7) is mounted on a mechanical stage (17) driven by two stepper motors (16) and which allows the entry slot to be displaced along the focal curve (6) to a new position (12). The angle of incidence ∈ (23) between grating normal (13) and the distance entry slot centre-grating centre change as a result. The equation known as the grating equation applies:

$$\lambda = \frac{\sin(\alpha) + \sin(\varepsilon)}{N * G} \quad \text{(Equ. 1)}$$

In which:
α is the angle of reflection
∈ is the angle of incidence
λ is the centre of the wavelength range (in mm) which falls through the exit slot
G is the number of grating grooves per mm
N is the order of diffraction.

The slot must have a spacing la from the centre of the grating $$la = R * \cos(\alpha) \quad \text{(Equ. 2)}$$

MEANING OF THE ADDITIONAL SYMBOLS

R diameter of the Rowland circle
la back focus (length of distance exit slot centre/grating centre)

With a given grating and fixed angle of reflection α (angle between grating normal and the distance exit slot centre-grating centre) the mean wavelength of the wave range passing through the exit slot thus changes with variation of ∈.

Figure 5:
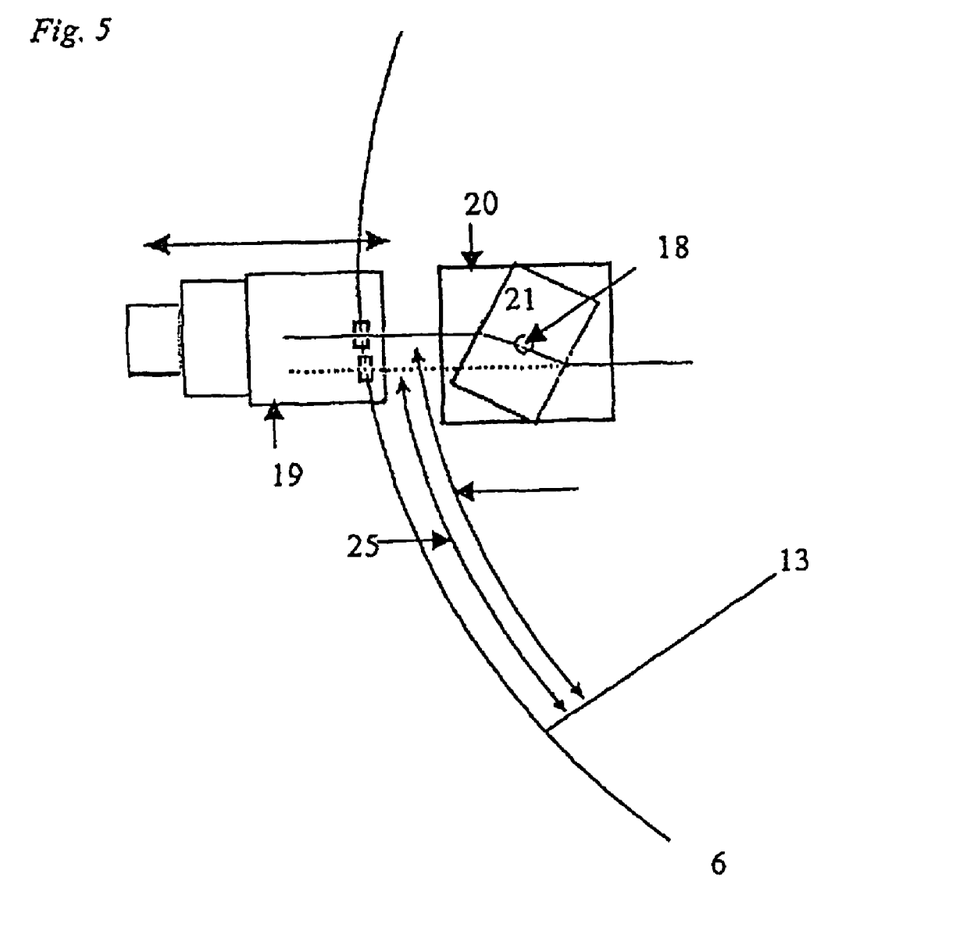
FIG. 5 illustrates an exemplary spectrometer with a changeable angle of incidence.

FIG. 5 illustrates how the angle of incidence ∈ (23) may also be changed with a plane-parallel quartz plate (refractor) rotatably mounted behind the entry slot.

To ensure software-controlled, precise rotation, the refractor (21) is secured to the shaft of a stepper motor (18).

Additional mechanisms allow displacement of the entry slot in the direction of the grating: the entry slot (7) is located on a linear feed (19) which is driven by a further stepper motor (20). This additional mechanism is only used in conjunction with the resolution correction, however.

After exiting the refractor the light distribution (14) passing through the entry slot appears displaced in a parallel manner by a distance δ. The beam accordingly has the same direction as it would have if—without refractor—it had passed through the entry slot (15) displaced on the focal curve. With refractor orientation perpendicular to the incident beam (23), the angle of incidence ∈ is changed to an angle of incidence ∈' (25). δ depends on the refractor thickness d, the refractive index of the refractor material n and the setting angle γ of the refractor:

$$\delta = d \sin\gamma \frac{(1 - \cos\gamma)}{\sqrt{n^2 - \sin^2\gamma}} \quad \text{(Equ. 3)}$$

(For derivation of the equation see Bergmann Schäfer, Lehrbuch der Experimentalphysik, Vol. III, Optik, de Gruyter, Berlin 1978, p. 40 ff).

A spectral range may accordingly be sequentially detected by incremental movement of the entry slot/rotation of the refractor with brief respective measuring time thereafter. The spectral lines that are to be measured should be located in the vicinity of the centre of the range of movement/rotation. It is expedient to select spectrally equidistant step sizes of the order of magnitude of the spectral slot width of the exit slot (for example step sizes of 5 pm). The individual measured values are sequentially stored. A field of measured values ordered according to wavelengths is accordingly obtained and can be treated like a field of measured values originating from a cohesive pixel range of optics with a multi-channel sensor.

If $\lambda_{Ri}$ designates the mean wavelength which passes through the i-th exit slot of the reference device R and $\lambda_{Gi}$ the mean wavelength which passes through the corresponding exit slot of a device G constructed in the same way, $\lambda_{Ri}$-$\lambda_{Gi}$ should be designated as the wavelength offset of the i-th exit slot of G.

The range of movement should accordingly be selected such that the detected wavelength range is large compared with the maximum wavelength offset that is to be expected. Suitable dimensioning for the range of movement with a maximum permitted wavelength offset of (0.1 nm is 1.1 nm. An overlapping wavelength range of at least 1 nm is therefore produced around each exit slot and is detected by both G and R.

Determination of the Wavelength Offset

The algorithm described in patent application DE 101 52 619 under the heading "Pixel offset" can accordingly be used to determine the wavelength offset. The term Pixel i used there should be replaced by the term measuring time i.

Suitable algorithms are also described in detail in the above-mentioned dissertation by the invent on pages 88 to 99 and 138 to 147.

Algorithm 1 discloses one of the algorithms described there which is based on the difference method.

---

Algorithm 1 Optimum offset with subtraction algorithm

TryOffset:= - Maximum Offset; MinError:=MaxReal;
Determining the difference for the offset which is
    determined by the control variables TryOffset
Errorsum:= 0;          // R[ ]: spectrum of the ref. device for
                         adjustment sample
i:= LeftEdge           // G[ ]: spectrum of the device for recalibrating
While(i<=RightEdge} and (Errorsum<MinError)
    Errorsum:=Errorsum + abs(R[i]−G|i+TryOffset1);    i:=i+1;
End// While –
If Errorsum<MinError
MinError:=Errorsum;    BestOffset:=TryOffset;
End// If
        TryOffset :=TryOffset + 1:
No
        Try Offset <= MaxOffset
                Yes
BestOffset accordingly contains the displacement in whole
    steps (measuring time numbers) which, applied to the
    spectrum of G, leads to a best possible overlapping of
        the spectra of R and G.

---

The difference in spectra of an exit slot of device G to be calibrated and reference device G are formed. Here the term

|R[1]−G[1+TryOffset]|+ . . . +|R[1]−G(1+TryOffset)| for −MaxOffset<TryOffset<MaxOffset is calculated. MaxOffset is set such that the maximum displacement that can be expected between exit slot of G and R can be recognized.

Figuratively speaking the algorithm therefore pushes the spectra one above the other and after each displacement step (TryOffset) obtains a total difference (ErrorSum) which states bow good the correspondence of this displacement is. The sought offset (BestOffset) in found if the spectra difference is minimal. It may be calculated from Equ. 1 to Equ. 3 and the Rowland diameter by how many mm the spectrum in the exit slot is displaced by this offset on displacement of the entry slot.

Determination and Correction of the Resolution

The lines of the adjustment sample which are located in the intersection of the spectral ranges detected by G and R around an exit slot $A_i$ can be used to compare the resolution of G and R. The half width is determined for all lines in this intersection. Ideally the half widths of the lines in the spectrum of G are equal to the half widths of the corresponding lines of R. The following causes may apply if there are differences:

1. The widths of the entry slots of G and R are not the same
2. The width of the considered exit slot of G and R is not the same
3. Entry or exit slots are not aligned exactly perpendicular to the focal plane
4. Entry and exit slots are not in focus The slot widths an be checked before assembly, for example by assessing the diffraction pattern in the laser light for dimensional accuracy. No other changes in the slot widths are to be expected over the life of the device. Changes in the slot widths do not have to be compensated within the framework of resolution correction therefore.

The upright position of the slots is ensured once by way of assembly using suitable teachings and checked in that when the upper slot half is covered, the spectrum coincides with the covered lower slot half. With expedient dimensioning of the slot carriers, the verticalness of the slots does not change during the life of the device either. Changes in the verticalness of the slots do not need to be compensated by the resolution correction therefore.

It should be noted that changes in width and verticalness cannot be corrected. If they occur, for example as transportation damage, they are recognized within the framework of the method outlined in Algorithm 2 (determination of optimum exit slot focal positions) however. In this case repair of the optical system is necessary.

The optical bank can expand or contract as a result of changes in temperature, whereby the slots mounted thereon remove themselves from or approach the grating. Changes in air pressure have a similar effect: increased air pressure displaces the focal curve toward the grating. Adjustment of the focal positions of entry and exit slots may therefore be sensible, particularly if an optical system is to be operated under atmospheric pressure over a wide temperature range and the optical bank, for example for weight reasons, is of such a nature that linear expansions of a few tenths of a millimeter can occur.

Example if the optical bank is made from aluminum the change in length with a change in temperature of 20° C. and a grating/slot spacing of 500 mm is approx. 0.27 mm.

To be able to determine the optimum exit slot position the entry slot must allow itself to be moved toward or away from the centre of the grating. The possible movement distance v in the grating direction is 1 mm. It should be maintained that small differences from the focal curve change the half widths only slightly. According to the invention a change in the line half widths of 10% (after intensity correction, see below) does not lead to any notable analysis errors. A depth of focus s may therefore be fixed by which a perfectly focused exit slot may be displaced without significantly broadening the spectrum taken up by it.

The slot defocusing for the exit slots $A_i$ of the device G may be determined using Algorithm 2 on the following page.

Here use is made of the fact that defocusings of an exit slot can be compensated by displacement of the entry slot. The following equation applies for Rowland circular gratings:

$$\frac{\cos^2(\alpha)}{la} - \frac{\cos(\alpha)}{R} \cdot \frac{\cos^2(\varepsilon)}{le} - \frac{\cos(\varepsilon)}{R} = 0 \qquad \text{(Equ. 4)}$$

In which:
R is the diameter of the Rowland circle
le in the entry focal intercept (length of the distance entry slot/grating centre)
la is the back focus (length of the distance exit slot centre/grating centre)
$\varepsilon$ is the angle of incidence (angle between distance entry slot centre/grating centre and grating normal)
$\alpha$ is the angle of emergence (angle between distance exit slot centre/grating centre and grating normal)

---

Algorithm 2: Determining the exit slot focal offset

```
//Initializations
For all exit slots Exit slots A_i
    Best_Slotwidth[i]:=Incorrect_Width
    Best_Focaloffset[i]:=0
End// For all-loops
//Determination of Focaloffset
Focalposition_Entryslot: =v/2
While Focalposition_Entryslot > -v/2
Move entry slot to Focalposition_Entryslot
Record the spectrum of the adjustment sample P around the
exit slot A_i and store it in partial spectrum[i]
Determine wavelength offset as described in the previous
paragraph
For all exit slots A_i
Determine the wavelength offset for exit slot A_i with help
Determine the wavelength range in which the spectrum
measured on G and the spectrum of the reference device
stored for the exit slot overlap
Calculate Mean_Linewidth in overlap region of measured
spectrum
If Best_Slotwidth[i]>Mean_Linewidth then
Best_Slotwidth[i]:=Mean_Linewidth
Best_Focaloffset[i]:=Focalposition_Entryslot
End // of the If block
End // of the For all-loop
Focalposition_Entryslot:=Focalposition_Entryslot - s
End // of the While loop
// Evaluation of the result
For all exit slots A_i
Calculate the mean line width that the lines in the
spectrum of the reference device around A_i have and
allocate the value Mean_Linewidth_Ref. Only lines from
the overlapping region are allowed to be taken into
account.
Tolerated_Linewidth:= Mean_Linewidth_Ref*Tolerancefactor
// Small excesses are tolerated
If Mean_Linewwidth>Tolerated_Linewidth then
Error message: resolution correction for exit slot i not
possible
Otherwise
Calculate the desired exit slot position using Equ. 4
End // If block
End // For all-loop
```

---

If an entry slot position is found in which, with the instantaneous position of the exit slot, the spectrum around this exit slot is optimally resolved, an exit slot position with optimum resolution may also be calculated for any other desired focal entry slot positions using Equ. 4.

If it is possible to focus the exit slot sufficiently accurately (i.e. with a difference less than s) under the pressure and temperature conditions that prevail during manufacture, subsequent air pressure and temperature fluctuations can largely be compensated by focusing of the entry slot.

Calculation Example

Rowland circular optics are equipped with a grating with a Rowland diameter of 750 mm and grating groove number G 2,700/mm. The angle of incidence is 30°. The optical bank is made from aluminum. The exit slot width is taken as 30 μm. The shortest wavelength to be measured is Fe 187.7 nm, the longest W 400.8 nm.

By using Equ. 1 and Equ. 2 the following angles and focal intercepts than result (spacings slot/centre of grating)

|  | Angle | Desired focal intercept |
|---|---|---|
| Entry slot | 30° | 649.5 |
| Exit slot Fe 187.7 nm | 0.4° | 750 |
| Exit slot Ni 471.4 nm | 35.6° | 609.8 |

At room temperature the slots are mounted exactly in accordance with the above angles and focal intercepts. If the temperature is increased by 20° C. the spacings between slot and centre of the grating increase owing to the thermal expansion of the optical bank.

The extension for the entry slot is 0.31 mm, 0.36 mm for the Fe exit slot and 0.29 mm for the Ni exit slot.

To make the nickel line sharp, according to Equ. 4 the entry slot must be displaced by 0.60 mm toward the centre of the grating. The entry focal intercept is then 649.23 mm.

The iron line is optimally sharp with a displacement of 0.666 mm and an entry focal intercept of 649.16 mm. The difference between the optimum for Fe and the optimum for Ni is low. If the mean is chosen—a displacement of 0.633 mm—, with Fe 187.7 nm and Ni 471.4 nm a respective defocusing of 0.033 mm then results according to Equ. 4. With Fe 187.7 nm the slot is located behind the focal curve by this amount; with Ni 471.4 by the same amount in front. The defocusing is lower for all exit slots between the two extremes. By using the intercept theorem it may be seen that, as a result of a defocusing D at an illumination width of the grating W, the slot widening v is approximately:

$$v = \frac{D * W}{la} \qquad \text{(Equ. 5)}$$

la again designates the back focus of the exit slot.

If the grating is illuminated 30 mm wide, according to Equ-5 the lot adversely widens from 30 to 31.3 μm. In practice such a small slot widening is no longer relevant.

The example shows that it is sufficient to correct the focus using the entry slot.

It should be noted that an unfavorable optical bank material has been assumed here. If the optical bank is made from steel the residual errors fall on less than half owing to the lower coefficient of linear expansion.

If individual focus adjustment of the exit slots is omitted, it is expedient to check the residual errors after focusing of the entry slot for each exit slot.

For each exit slot $A_i$ Algorithm 2 calculates an optimum entry slot position of optimum resolution. If the exit slots are correctly assembled the optimum entry slot positions must lie close together over a wide temperature range. In our example the maximum differences between entry slot position to be adjusted and optimum entry slot position is less than 0.034 mm for any desired exit slot. If a greater difference is found, the exit slots are not correctly focused. This check is part of the calibration capacity check. Immediately after device production it may be ascertained whether all exit slots are correctly assembled. Throughout the life of the device the position of the exit slots with respect to the focal curve should no longer change under the same temperature and pressure conditions.

The control algorithm should nevertheless be run through with each calibration adjustment in order to be able to detect error states, as are caused for example by mechanical damage.

Step 2—Adjusting the Slot Positions

The following parameters were calculated in step 1:
a signed distance by which the entry slot is to be displaced along the focal curve
a signed distance by which the entry slot is to be displaced in the grating direction
for each exit slot a signed distance for a displacement along the focal curve In addition step 1 provided the statement as to whether it is possible to set the slots such that the same wavelength ranges with the same resolution fall through the exit slots of device G as with a reference device R, from which the calibrations are to be taken over. Only if this is the case can calibrations be transmitted from R to G. The check is part of the assessment of calibration capacity of G.

Two variants of mechanism for adjusting the entry slot positions have already bee presented in step 1. According to the mechanism illustrated in FIG. 4 the entry slot (7) is moved to the desired position via a mechanical stage (17) driven by stepper motors.

Alternatively, a mechanism for entry slot positioning is presented in FIG. 5 which, instead of displacing the entry slot along the focal curve, produces the angle of incidence by rotation of a retractor. Focusing (displacement in the grating direction) is achieved by moving the slot of a linear feed (19) which carries the entry slot (7).

It should be noted that stepper motors with step angles less than 0.9° are not common. In order to nevertheless be able to implement the required number of measuring positions using the refractor stepper motor, it may be necessary to connect a gearing with high reduction ratio downstream of the stepper motor and to assemble the refractor on the driven shaft of the gearing.

Figure 6:
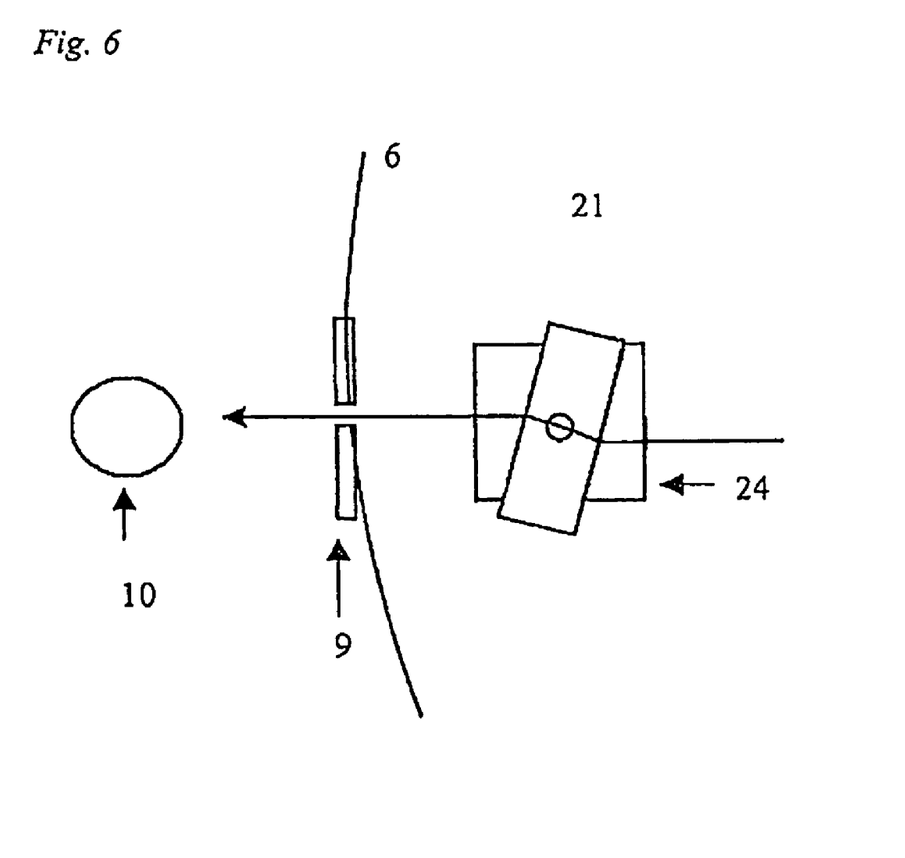
FIG. 6 illustrates an exemplary spectrometer with adjustable slot positions.

As described under step 1, it must be possible to implement a movement along the focal curve for each exit slot in order to be able to compensate the errors of the relative exit slot positions as have been calculated in step 1. The traversing range of this movement is small compared with the traversing range of the entry slot and, as already mentioned above, is of the order of magnitude of 0.1 mm. FIG. 6 shows one possible embodiment. A refractor (21) is assembled on the shaft of a servomotor (24) and is rotated by it. Alternatively, a stepper motor may be used although servomotors have the advantage that they may be obtained in small designs at reasonable prices. Moreover they conventionally allow absolute positioning, the positioning being brought about by application of an alternating voltage, of which the pulse/pause ratio reflects the position to be adjusted.

Possibilities of direct positioning of the exit slot may be achieved using piezo actuators, galvanometers and temperature-controlled bimetallic strips. Displacement of exit slots via a linear feed along the focal curve is also possible.

Step 3—Intensity Corrector

At the end of step 2 it is ensured that the same wavelength ranges with the same resolution pass through the exit slots of the device G for calibrating as in the case of the reference device R, the calibrations of which are to be taken over. However this is not to say that, for a given sample and identical adjustment of the excitation source, the measured light distribution intensities are the same in the case of G and R. The reasons for this are differences in the optical conductances of transparent components, manufacturing tolerances in the case of grating diffraction efficiencies, effects of dirt and differences in the sensitivity of the sensors.

The simplest method of intensity correction comprises a two-point recalibration for each groove (groove should be taken to mean the exit slot/sensor unit) as is conventionally used to again bring grooves of individually calibrated devices to the intensity level at the calibration instant.

A set of recalibration samples should be compiled in such a way that two samples are associated with each groove.

One of the samples has a concentration that is in the lower third of the grove work area; the concentration of the second sample is in the upper third of the working groove. A linear function is calculated (see Algorithm 3).

---

Algorithm 3 Determining a recalibration straight line for intensity correction

//Tdesired[i] value for low sample for i-th exit slot, measured on R
//Hdesired[i] value for high sample for i-th exit slot, measured on R
//Tactual[i] value for low sample for i-th exit slot, measured on G
//Hactual[i] value for low sample for i-th exit slot, measured on G
//Factor[i] factor of recalibration straight line for slot i
//Offset[i] offset of recalibration straight line for slot i
For all exit slots i
    Factor[i]: = (Hdesired[i]−Tdesired[i])/(Hactual[i]−Tactual[i]);
    Offset[i]: = (Hdesired[i]*Tactual[i]−Hactual[i]*Tactual[i]/(Tactual[i]−Hactual[i];
End

---

The raw measured values, measured on G, of the i-th exit slot MW|i| are then converted according to formula $$MWCorr|i|:=MW|i|*Factor|i|\uparrow Offset|i| \quad (Equ.\ 6)$$

into measured values MWCorr|i| which correspond to the intensity level of G.

However, the method has a serious drawback: only one low sample and one high sample actual value are measured for each exit slot and it is assumed that the intensities of G may be converted into those of R by means of a linear function. This assumption is also usually correct. Malfunctions of G are not detected, however.

An example of this: The electronic measuring devices (integrators) of R and G are capable of detecting measured values up to 1,000,000. For a groove i a low sample value of 80,000 and a high sample value of 800,000 are measured on R. G is twice as fast. 160,000 is accordingly measured on G for the low sample but owing to the saturation limit only 1,000,000 is measured for the high sample. Instead of a factor of 0.5 and an offset of 0, a factor of 0.86 and an offset of −57,140 are calculated. A further potential error, which is not detected when using algorithm 3, is a non-linearly measuring electronic device in device G.

It is therefore more advantageous to use a method analogous to that presented in patent application DE 101 52 679 for optics with multi-channel sensors. Algorithm 4 outlines this method. The spectrum around the exit slot normal position is detected by moving the entry slot. From step 2 it is known between which entry slot extreme positions of G wavelengths may be measured which also exist with R. As mentioned above, a range of typically 1 nm thus results, which, with movement steps of 5 pm, is covered in 200 steps. A plurality of spectral lines is located in this range with suitable selection of the adjustment sample. A measurement is carried out at each of the 200 positions. A measuring time need only integrate a few sparks. However it is important to ensure that a measuring time always consists of the same number of sparks. The corresponding intensities of the spectrum of G and the spectrum of R are then plotted against each other. If optics, excitation generator and electronic measuring device of G are functioning, all points should lie in the vicinity of a straight line which runs through the point (0,0). The course of the recalibration straight line is determined by way of a linear regression. Residual scattering, inclination and offset must not exceed predefined limits. Checking these limits is part of the calibration capacity check. It should be noted that differences in the excitation parameters between G and R lead to an increased residual scattering. The cause lies in the fact that even closely adjacent lines react very differently to a change in excitation current and duration. However, as mentioned above, a plurality of spectral line are located within the range of movement. The topic is dealt with in detail on page 127 ff. of the inventor's dissertation.

For all measuring points m in the spectrum of the i-th exit slot of G which have a corresponding measuring point in the spectrum of the i-th exit slot of R:

Form number pair for corresponding data points from G and R;

Carry out a linear regression over the quantity of this pair;
If residual scattering of the regression calculation>maximum residual scattering ---
Algorithm 4: intensity corrector Output error message, device G cannot be calibrated
otherwise
Store factor and offset for exit slot i
end// If ..
End// For ..

---

The intensities measured on G are converted into the level of device R by again applying Equ. 6

Once the parameters of the intensity correction have been calculated, the entry slot is again moved to the position determined in step 1. The device G is accordingly ready to measure unknown samples. After the raw measured values have been recorded they should be inserted in Equ. 6. The result is identical measured values which R would also provide far the same sample. The calibration of R may thus be used.

Spectrometer Optics Comprising Positionable Slots and Method for the Fully Automatic Transmission of Calibrating Adjustments Between Spectrometers Equipped with Optics of This Type

LIST OF REFERENCE NUMERALS (1) support
(2) sample
(3) counter electrode
(4) excitation generator
(5) optical system
(6) focal curve
(7) entry slot
(8) concave grating
(9) exit slot
(10) multiplier phototube
(11) multi-channel sensor
(12) new entry slot position
(13) grating normal
(14) light distribution passing through entry slot
(15) displaced entry slot position
(16) stepper motors
(17) mechanical stage
(18) stepper motor shaft
(19) linear feed
(20) stepper motor
(21) refractor
(22) entry slot region
(23) angle of incidence $\epsilon$
(24) servo motor
(25) changed angle of incidence $\epsilon'$
(26) distance exit slot/grating centre
(27) direct light distribution path or fiber optic

The invention claimed is:

1. A method for calibrating spectrometer systems comprising sensors without spatial resolution, characterized by the following steps:
   a. determining a device-independent calibration function $K_u$ on a reference spectrometer R;
   b. transmitting the device-independent calibration function $K_u$ to a spectrometer G to be calibrated;
   c. determining a respective displacement vector for an entry slot and exit slots of the spectrometer G;
   d. moving the entry slot and the exit slots into desired positions as a function of the displacement vectors;
   e. determining an intensity correction function which, after positioning of the entry slot and the exit slots, allows raw intensities for any desired sample P measured on a spectrometer G to be converted such that they match raw intensities for P measured on a reference device R.

2. The method as claimed in claim 1, further comprising:
changing the angle of incidence of optics and using environment information thus obtained to calculate a vector $K'_G$ that describes the state of the spectrometer G.

3. The method as claimed in claim 1, further comprising:
displacing the entry slot and the exit slots as a function of a vector $K'_G$, which contains desired positions for the entry slot and exit slots, such that same spectral segments pass through the exit slots of optics $O_G$ of the spectrometer G as through corresponding exit slots of optics $O_R$ of the reference device R.

4. The method as claimed in claim 1, characterized in that for each exit slot of the spectrometer G, a vector $K'_G$ contains coefficients of an intensity transmission polynomial which, after positioning of the entry slot and the exit slots, allows the raw intensities measured for the desired sample P on the spectrometer G to be converted such that they match the raw intensities for P measured on the reference device R.

5. The methods as claimed in claim 1, further comprising assessing a calibration capacity to calculate a vector $K'_G$ for spectrometer G.

* * * * *